(12) United States Patent
Miki et al.

(10) Patent No.: US 10,132,779 B2
(45) Date of Patent: Nov. 20, 2018

(54) EDDY CURRENT INSPECTION DEVICE

(71) Applicant: Hitachi-GE Nuclear Energy, Ltd., Hitachi-shi, Ibaraki (JP)

(72) Inventors: Masahiro Miki, Tokyo (JP); Soushi Narishige, Tokyo (JP); Isao Yoshida, Hitachi (JP)

(73) Assignee: Hitachi-GE Nuclear Energy, Ltd., Hitachi-shi (JP)

( * ) Notice: Subject to any disclaimer, the term of this patent is extended or adjusted under 35 U.S.C. 154(b) by 59 days.

(21) Appl. No.: 15/163,841

(22) Filed: May 25, 2016

(65) Prior Publication Data

US 2016/0356743 A1  Dec. 8, 2016

(30) Foreign Application Priority Data

Jun. 3, 2015 (JP) ................................. 2015-113521

(51) Int. Cl.
  *G01N 27/90* (2006.01)
(52) U.S. Cl.
  CPC ....... *G01N 27/9053* (2013.01); *G01N 27/902* (2013.01); *G01N 27/904* (2013.01)
(58) Field of Classification Search
  CPC .... G01N 27/9053; G01N 27/82; G01N 27/83; G01N 27/90; G01N 27/9013;
  (Continued)

(56) References Cited

U.S. PATENT DOCUMENTS 4,742,298 A * 5/1988 Ando ................. G01N 27/9046
  324/220
5,047,719 A * 9/1991 Johnson ............. G01N 27/9033
  324/242

(Continued)

FOREIGN PATENT DOCUMENTS

JP        8-334498 A    12/1996
JP    2003-344360 A    12/2003

(Continued)

OTHER PUBLICATIONS

Extended European Search Report issued in counterpart European Application No. 16169759.4 dated Nov. 7, 2016 (nine (9) pages).

(Continued)

*Primary Examiner* — Tung X Nguyen
*Assistant Examiner* — Robert P Alejnikov, Jr.
(74) *Attorney, Agent, or Firm* — Crowell & Moring LLP (57) ABSTRACT

To realize an object of providing an eddy current inspection device which is able to control a sensitivity decrease, and is able to reliably detect a defect. An eddy current inspection device of the present invention is provided with an orthogonal detection mode which measures an electromotive force signal using a coil pair which is configured by two coils within the first row coil group, a first intersection detection mode which measures the electromotive force signal using the first coil pair which is configured by the two coils within the first row and second row coil groups that are lined up in a direction which intersects with the scanning direction, and a second intersection detection mode which measures the electromotive force signal using the second coil pair which is configured by the two coils within the first row and second coil groups that are lined up in a direction in which a direction which intersects with the scanning direction is on the same side as the direction through which the first coil pair intersects and has a larger coil pair intersection angle than the coil pair intersection angle of the first coil pair.

5 Claims, 9 Drawing Sheets

(58) Field of Classification Search
CPC ........... G01N 27/9026; G01N 27/9033; G01N 27/904; G01N 27/9046; G01N 27/902; B65G 43/02; G01R 31/34; G01R 15/181
USPC .................................................. 324/240–242
See application file for complete search history.

(56) References Cited

U.S. PATENT DOCUMENTS

| | | | |
|---|---|---|---|
| 6,344,739 B1* | 2/2002 | Hardy | G01N 27/902 324/220 |
| 7,560,920 B1* | 7/2009 | Ouyang | G01N 27/902 324/240 |
| 2006/0132123 A1* | 6/2006 | Wang | G01N 27/902 324/239 |
| 2012/0176124 A1* | 7/2012 | Szulyk | G01B 7/003 324/207.18 |
| 2013/0106409 A1* | 5/2013 | Wang | G01R 33/028 324/239 |
| 2013/0193960 A1* | 8/2013 | Nishimizu | G01N 27/9006 324/240 |

FOREIGN PATENT DOCUMENTS

| | | |
|---|---|---|
| JP | 2010-281765 A | 12/2010 |
| JP | 2011-33510 A | 2/2011 |
| JP | 2012-2632 A | 1/2012 |
| WO | WO 00/47986 A1 | 8/2000 |

OTHER PUBLICATIONS

Cover page of EP 1 153 289 A0 published Nov. 14, 2001 (one (1) page).

English-language translation of JP 8-334498 A previously submitted as document B1 in an IDS filed on May 25, 2014 (fourteen (14) pages).

* cited by examiner

FIG. 11B

EDDY CURRENT INSPECTION DEVICE

TECHNICAL FIELD

The present invention relates to an eddy current inspection device.

BACKGROUND ART

The eddy current inspection device is widely utilized to carry out defect inspection of a structure which is formed of a conductive material. The eddy current inspection device generates an eddy current within the structure which is an inspection target using an excitation coil and detects the defect by detecting a change of the eddy current in the vicinity of the defect using a detection coil.

For example, such an eddy current inspection device is known in which a plurality of eddy current sensors in a sensor body are arranged in a zig-zag shape in a flaw detection movement direction, and which carries out flaw detection by switching while selecting a sensor pair formed from two sensors that are disposed lined up in at least two directions that intersect with the flaw detection movement direction from a plurality of sensors (for example, refer to PTL 1).

In the eddy current inspection device, it is possible to measure the eddy current in two directions which intersect by selectively switching the sensor pair of two directions which intersect with the flaw detection movement direction, and it is possible to reduce a sensitivity difference with respect to a direction of the defect in comparison to the device in which the sensor pair is arranged in only one direction.

CITATION LIST

Patent Literature

PTL 1: JP-A-8-334498

SUMMARY OF INVENTION

Technical Problem

However, even in a case where a device in the related art as described above is used, in a case where a maximum defect intersection angle is increased, in a case where a sensitivity change increases with respect to the direction of the defect due to an influence, for example, of a material property (electromagnetic characteristic such as conductivity), or the like, it is not necessarily possible to reliably detect the defect due to a decrease in sensitivity.

Figures 4A, 4B:
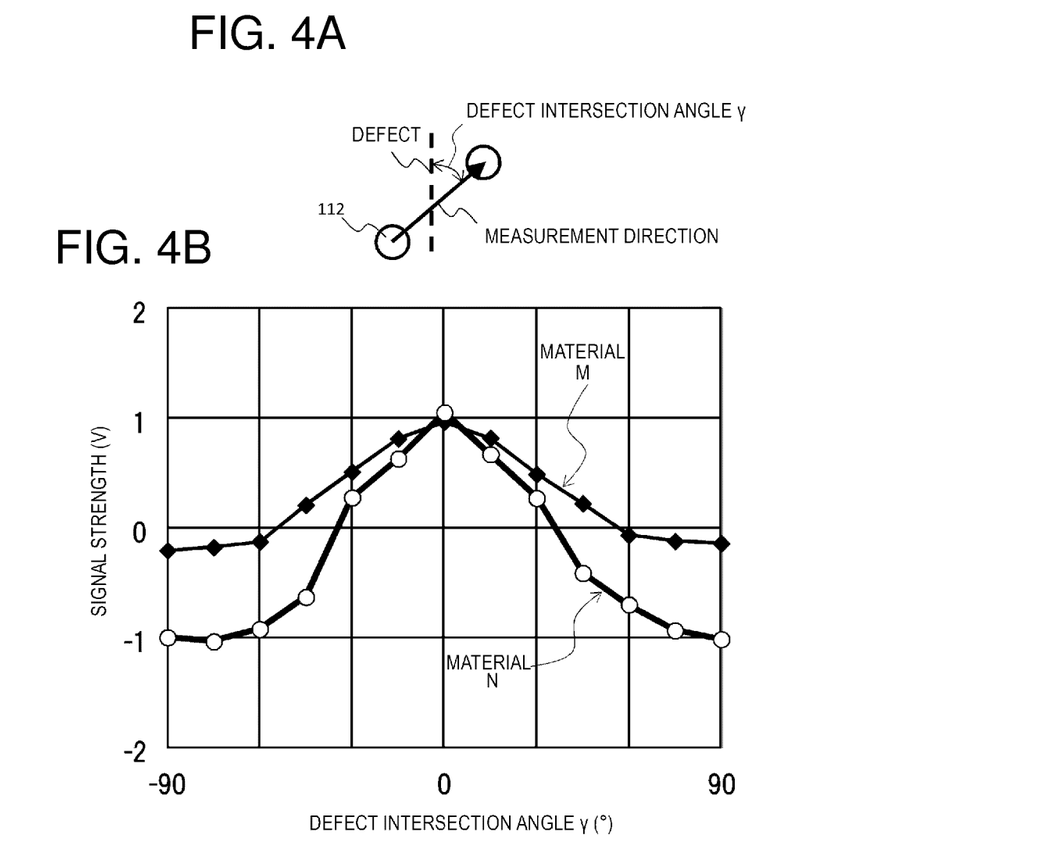

For example, in a case where two subjects are measured that are formed of materials M and N in which the sensitivity changes are different from each other as shown in FIG. 4(b), the sensitivity change of material N increases in comparison to material M, and with respect to the material M in which the intersection angle where a signal intensity of an electromotive force signal is 0 is approximately 55°, in material N, the angle is approximately 35°. For this reason, in a case of carrying out flaw detection using the eddy current inspection device in which a plurality of coils are arranged in a zig-zag shape of an equilateral triangle (maximum intersection angle 30°) as in the related art, there is a concern that it is not possible to reliably detect the defect as a result of the electromotive force signal rapidly decreasing when the defect intersection angle increases in measurement of the subject which is formed of material N, and of not being able to obtain the electromotive force signal with sufficient strength in a state in which the defect intersection angle is in the vicinity of the maximum defect intersection angle.

The present invention is carried out in consideration of the above circumstances, and an object thereof is to provide an eddy current inspection device which is able to control a sensitivity decrease, and is able to reliably detect a defect.

Solution to Problem

The present invention relates to (1) An eddy current inspection device including a multi-coil probe which has a first row coil group made from a plurality of coils which are lined up in a linear direction which is orthogonal to a scanning direction and a second row coil group made from a plurality of coils which are lined up so as to be parallel to the first row coil group, an orthogonal detection mode which measures an electromotive force signal using a coil pair which is configured by two coils within the first row coil group, a first intersection detection mode which measures the electromotive force signal using a first coil pair that is configured by two coils within the first row and second row coil groups that are lined up in a direction which intersects with the scanning direction, and a second intersection detection mode which measures the electromotive force signal using a second coil pair which is configured by two coils within the first row and second coil groups that are lined up in a direction in which a direction that intersects with the scanning direction is on the same side as the direction through which the first coil pair intersects and has a larger coil pair intersection angle than the coil pair intersection angle of the first coil pair, (2) The eddy current inspection device in (1) including a signal intensity compensation section which performs predetermined correction according to a gap between the two coils which configure the coil pair with respect to the electromotive force signal, (3) The eddy current inspection device in (1) or (2) including a signal intensity measurement section which determines presence or absence of a defect using a maximum value of the signal intensity of the electromotive force signal and a predetermined reference value, (4) The eddy current inspection device in any one of (1) to (3) including a signal phase evaluation section which determines presence or absence of the defect using a phase angle of the electromotive force signal with respect to the reference signal, (5) The eddy current inspection device in any one of (1) to (4) in which the coils in the first row and second row coil groups are disposed in a zig-zag shape in planar view, and (6) The eddy current inspection device in any one of (1) to (5) in which a maximum defect intersection angle is accommodated in a range of a single defect intersection angle that does not contain a defect intersection angle in which the signal intensity of the electromotive force signal with respect to the defect is zero.

Here, "electromotive force signal" has a meaning of a signal of electromotive force which is measured using the coil pair, and "control signal" has a meaning of a signal which is input in a subject using the coil pair. In addition, "coil pair intersection angle" has a meaning of an angle that has an arrangement direction (hereinafter referred to as "first coil pair direction" and the like corresponding to the coil pair) of two coils which configure a coil pair with respect to the scanning direction of the multi-coil probe. In addition, "defect intersection angle" has a meaning of an angle which has a coil pair direction and a longitudinal direction of the defect, and "maximum defect intersection angle" has a meaning of a maximum value of the defect intersection angle at which the coil pair is able to take that is the smallest defect intersection angle out of the coil pair which is used in the orthogonal detection mode, the first intersection detection mode, and the second intersection detection mode. In addition, in a case where it is assumed that a straight line along the coil pair direction is a straight line passing through the origin of the orthogonal coordinate system, "a direction which intersects with the scanning direction is on the same side as the direction through which the first coil pair intersects" has a meaning of an aspect in which a straight line which is different from the straight line passing through the origin of the orthogonal coordinate system is present in the same quadrant as the straight line.

Advantageous Effects of Invention

The present invention is able to provide an eddy current inspection device which is able to suppress a sensitivity decrease, and is able to reliably detect a defect.

BRIEF DESCRIPTION OF DRAWINGS

FIG. 2 shows schematic enlarged views of a multi-coil probe in FIG. 1, in which FIG. 2A indicates a front surface view and FIG. 2B indicates a planar view.

FIG. 4 shows schematic diagrams illustrating a change of signal intensity with respect to a defect intersection angle, in which FIG. 4A indicates a description of the defect intersection angle and FIG. 4B indicates an example of a relationship of the defect intersection angle and the signal intensity of an electromotive force signal.

FIG. 9 shows schematic explanatory diagrams of a Lissajous waveform which is obtained using the eddy current inspection device in FIG. 1, in which FIG. 9A indicates an example of the electromotive force signal due to the defect and FIG. 9B indicates an example of the electromotive force signal due to lift-off.

FIG. 11 shows schematic enlarged views of the multi-coil probe in the eddy current inspection device according to a second embodiment of the present invention, in which FIG. 11A indicates a planar view and FIG. 11B indicates a front surface view.

DESCRIPTION OF EMBODIMENTS

An eddy current inspection device of the present invention is provided with a multi-coil probe which has a first row coil group made from a plurality of coils which are lined up in a linear direction which is orthogonal to a scanning direction and a second row coil group made from a plurality of coils which are lined up so as to be parallel to the first row coil group, including an orthogonal detection mode which measures an electromotive force signal using a coil pair which is configured by two coils within the first row coil group, a first intersection detection mode which measures the electromotive force signal using the first coil pair which is configured by two coils within the first row and second row coil groups that are lined up in a direction which intersects with the scanning direction, and a second intersection detection mode which measures the electromotive force signal using the second coil pair which is configured by two coils within the first row and second coil groups that are lined up in a direction in which a direction which intersects with the scanning direction is the same side as the direction through which the first coil pair intersects and has a larger coil intersection pair angle than the coil intersection pair angle of the first coil pair.

By providing the orthogonal detection mode, the first intersection detection mode, and the second intersection detection mode, the eddy current inspection device is able to reduce a maximum defect intersection angle and is able to reliably detect a defect in comparison to the eddy current inspection device which is provided with only the orthogonal detection mode and the first intersection detection mode.

First and second embodiments of the eddy current inspection device are described below with reference to FIGS. 1 to 11, but the present invention is not limited only to the embodiments described in the drawings.

Here, in the embodiment, a case is described below in which a subject with a plate form is inspected as an inspection target. In addition, for convenience, the longitudinal direction of the multi-coil probe is an X direction, the scanning direction of the multi-coil probe is a Y direction, and a direction which is orthogonal to the X direction and the Y direction is a Z direction.

In addition, in the present specification, "defect" has a meaning of a geometric specific site (flaw) such as a crack.

First Embodiment

Figure 1:
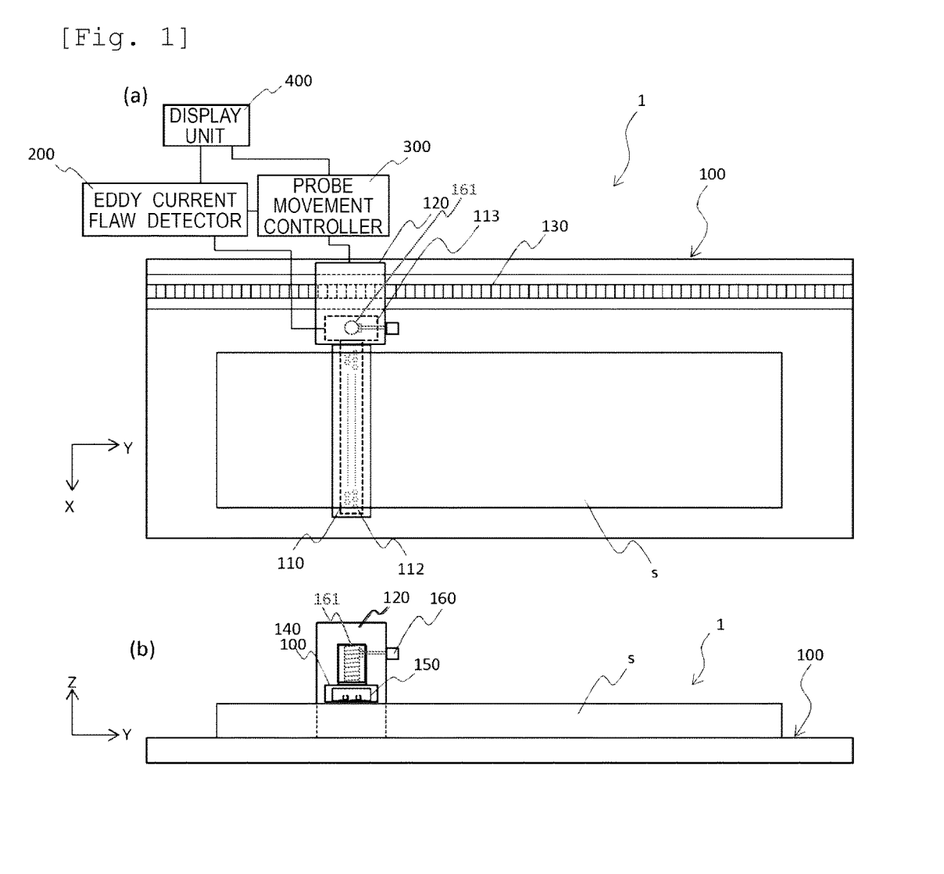
FIG. 1 shows schematic configuration views of the eddy current inspection device according to a first embodiment of the present invention, in which FIG. 1A indicates a planar view and FIG. 1B indicates a front surface view.

FIG. 1 shows schematic configuration views of the eddy current inspection device according to a first embodiment of the present invention. As shown in FIG. 1, an eddy current inspection device 1 is schematically configured by a main body 100, an eddy current flaw detector 200, a probe movement controller 300, and a display unit 400.

The main body 100 is provided with a multi-coil probe 110, a probe movement unit 120, a guide rail 130, a probe pressing jig 140, a buffer material 150, and a pressing adjustment screw 160.

Figure 2A:
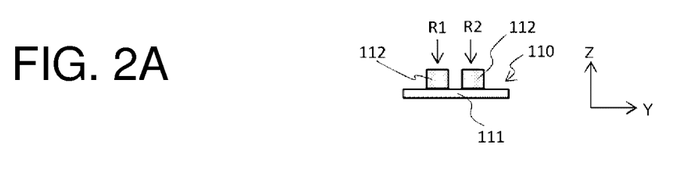
Figure 2B:
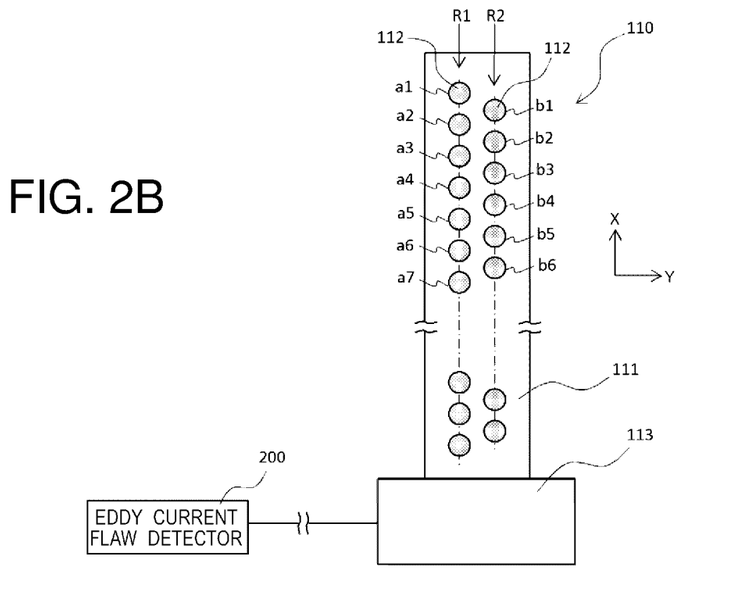

As shown in FIG. 2, the multi-coil probe 110 has a first row coil group R1 which is formed from a plurality of coils 112 which are lined up in a linear direction (X direction) which is orthogonal to the scanning direction (Y direction) and a second row coil group R2 which is formed from a plurality of coils 112 which are lined up so as to be parallel to the first row coil group R1. The coils 112 which configure the first row and second row coil groups R1 and R2 perform both actions of exciting eddy current within a subject s, and detecting a change of an eddy current distribution in a surface section of the subject s. Below, the coil 112 which excites the eddy current within the subject s is an "excitation coil", and the coil 112 which detects the change of the eddy current distribution in a surface section of the subject s is a "detection coil". Here, the coil 112 which configures the first row coil group R1 is referred to as coil a1, coil a2, . . . in order from on a paper surface. Here, the coil 112 which configures the second row coil group R2 is referred to as coil b1, coil b2, . . . in order from on the paper surface.

The coils 112 in the first row and second row coil groups R1 and R2 are disposed in a zig-zag shape which is shifted by a half pitch from each other in planar view. In this manner, it is possible to increase the signal intensity of the electromotive force signal by reducing the maximum defect intersection angle and it is possible to further reliably detect the defect, by disposing the coils 112 in the zig-zag shape. As the coil disposition of the zig-zag shape, the disposition in the zig-zag shape in which the coils 112 that configure the first row coil group R1 and the coils 112 that configure the second row coil group R2 are shifted from each other at a half pitch is preferable, and a disposition is further preferable in which each coil 112 which is disposed in the zig-zag shape that is shifted from each other at a half pitch is positioned at each vertex in a virtual equilateral triangle. Thereby, it is possible to reduce the maximum defect intersection angle, and it is possible to more reliably detect the defect.

In addition, it is also preferable that the maximum defect intersection angle is within a range of a single defect intersection angle in which the defect intersection angle in which the signal intensity of the electromotive force signal with respect to the defect is zero is not included. In this manner, it is possible to avoid the signal intensity of the electromotive force signal is zero regardless of there being a defect and it is possible to detect the defect more reliably, by the maximum defect intersection angle being in the range above.

In detail, the multi-coil probe 110 further has a substrate 111 on which the coil 112 is fixed and wiring is electrically formed, and a multiplexer circuit section 113 which performs selection and switching of the coil 112 which detects the change of the eddy current signal. The substrate 111, the coil 112, and the multiplexer circuit section 113 are electrically connected by wire, and the multiplexer circuit section 113 is connected to the eddy current flaw detector 200 which will be described later. A switching program of the excitation coil and the detection coil according to the detection mode is stored in the multiplexer circuit section 113, and the eddy current is measured by operating the program by an instruction from the eddy current flaw detector 200. Here, it is preferable that the substrate 111 is formed of a material that has flexibility. Thereby, when a curved surface section is measured, it is possible to increase adhesiveness of the subject s.

The probe movement unit 120 holds the multi-coil probe 110, and the multi-coil probe 110 is moved in parallel to the scanning direction with respect to the subject s. The probe movement unit 120 has a wheel (not shown in the drawings) which moves along the guide rail 130, a motor (not shown in the drawings) which moves the wheel, and an encoder (not shown in the drawings) which measures the amount of movement of the multi-coil probe 110, and performs measurement by moving the multi-coil probe 110 in parallel to the Y direction (scanning direction). Movement control of the probe movement unit 120 is performed by the probe movement controller 300 which will be described later.

The guide rail 130 supports the probe movement unit 120 so as to be able to move in parallel. The probe pressing jig 140 abuts the multi-coil probe 110 on the subject s at a fixed pressing force. The buffer material 150 is formed of a sponge or the like, and the pressing force of the multi-coil probe 110 on the subject s is uniformized. The pressing adjustment screw 160 adjusts the pressing force of the multi-coil probe 110. In the pressing adjustment screw 160, the vertical position of the probe moving unit 120 can be adjusted by the ball screw mechanism 161. These mechanisms bring the probe moving unit 120 into contact with the subject and adjust the pressing force of the multi-coil probe 110.

Figure 3:
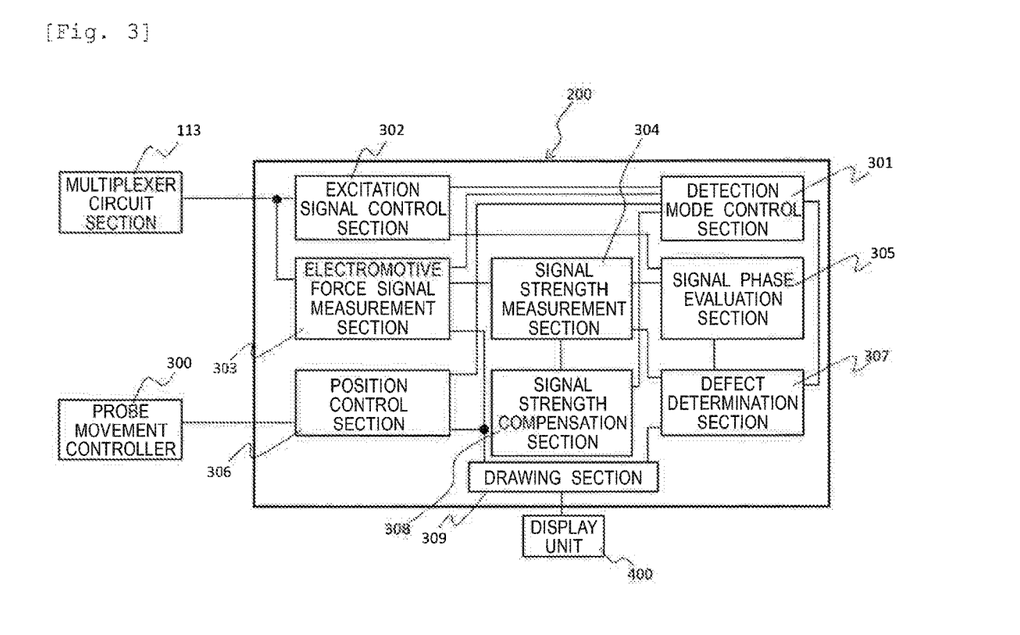
FIG. 3 is a schematic block diagram illustrating a configuration of an eddy current flaw detector in FIG. 1.

The eddy current flaw detector 200 inputs the electromotive force signal which is measured by the detection coil, acquires the flaw detection signal from within the electromotive force signal, and outputs the signal as the digital signal via the A/D converter. In outline, as shown in FIG. 3, the eddy current flaw detector 200 is configured by a detection mode control section 301, an excitation signal control section 302, an electromotive force signal measurement section 303, a signal intensity measurement section 304, a signal phase evaluation section 305, a position control section 306, a defect determination section 307, a signal intensity compensation section 308, and a drawing section 309.

The detection mode control section 301 selects a detection mode from the orthogonal detection mode, the first intersection detection mode, and the second intersection detection mode, and transmits a signal which relates to the detection mode to the excitation signal control section 302, the electromotive force signal measurement section 303, and the signal intensity compensation section 308. In addition, the detection mode control section 301 sends a movement instruction of the probe movement unit 120 to the position control section 306 and receives the amount of movement.

The excitation signal control section 302 receives a signal from the detection mode control section 301, and designates the excitation coil and receives the excitation coil to the multiplexer circuit section 113. The electromotive force signal measurement section 303 receives the signal detected by the multi-coil probe 110 from the multiplexer circuit section 113, and transmits to the signal intensity measurement section 304 and the drawing section 309. Here, detection is continuously performed by the excitation of the excitation coil and detection coil in the multi-coil probe 110. In addition, when measurement of the electromotive force signal is ended in all detection modes, the electromotive force signal measurement section 303 sends the signal of the end of measurement at the position in the detection mode control section 301.

The signal intensity measurement section 304 stores the reference signal which is acquired in advance by measurement of the defect (hereinafter referred to as "reference defect") which is a reference that is used in order to calibrate the eddy current inspection device 1, and determines presence or absence of the defect using the maximum value of the signal intensity and a predetermined reference value of the electromotive force signal which is measured by the detection coil. In this manner, the eddy current inspection device 1 is able to uniformly determine the defect by having the signal intensity measurement section 304.

The signal phase evaluation section 305 stores the reference signal which is acquired in advance by the measurement of the reference defect, and determines presence or absence of a defect using a phase angle of the electromotive force signal with respect to the reference signal. In this manner, the eddy current inspection device 1 is able to determine the origin of the electromotive force signal and is able to more reliably detect the defect by having the signal phase evaluation section 305.

The position control section 306 receives a signal from the detection mode control section 301, sends a movement instruction of the probe movement unit 120 to the probe movement controller 300 and stores the amount of movement, and transmits the amount of movement which is stored to the detection mode control section 301 and the drawing section 309. In addition, the defect determination section 307 evaluates the electromotive force signal based on the evaluation result of the signal intensity measurement section 304 and the signal phase evaluation section 305, and the evaluation result is transmitted to the drawing section 309.

The signal intensity compensation section 308 performs predetermined correction according to a gap of two coils which configure the coil pair with respect to the measured electromotive force signal. In this manner, the eddy current inspection device 1 is able to compensate a sensitivity difference of a signal due to difference of a coil gap in each detection mode and is able to detect the defect with good precision by having the signal intensity compensation section 308. Here, in the present embodiment, implementation of three detection modes are exemplified, but since a gap between the excitation coil and the detection coil is different in each detection mode, the difference is generated in a level of the electromotive force signal in each detection mode. Here, a coefficient is multiplied by a signal intensity which is measured by the signal intensity measurement section 304 according to the coil gap in the detection mode using the signal intensity compensation section 308 and compensates for the sensitivity difference. The signal which is compensated by the signal intensity compensation section 308 is replied to the signal intensity measurement section 304. In addition, the drawing section 309 accumulates and records the output (inspection result) from the electromotive force signal measurement section 303, the position control section 306, and the defect determination section 307, and transmits the inspection result to the display unit 400.

Here, for example, as the eddy current flaw detector 200, it is possible to use a general-purpose arithmetic processing device such as a personal computer. In a case where the arithmetic processing device is used as the eddy current flaw detector 200, the arithmetic processing device may be a single device, and may be a plurality of devices that share the arithmetic processing.

The probe movement controller 300 controls the movement of the probe movement unit 120. The probe movement controller 300 stores the amount of movement of the probe movement unit 120, and the amount of movement is transmitted to the detection mode control section 301 and the drawing section 309.

The display unit 400 displays the inspection result which is received from the drawing section 309. For example, the display unit 400 is able to adopt a monitor and the like of a two-dimensional display and the like. For example, the inspection result is displayed on the monitor as a two-dimensional image in association with the measurement position.

Next, a detection mode and a defect determination method using the eddy current inspection device 1 of the configuration described above is described in detail.

[Detection Mode]

As described above, since the signal intensity is changed due to the defect intersection angle, material properties (electromagnetic properties such as conductivity), and the like (refer to FIG. 4(b)), setting the detection mode such that the maximum defect intersection angle is reduced as much as possible is important in order to improve defect identifying characteristics.

Figure 5:
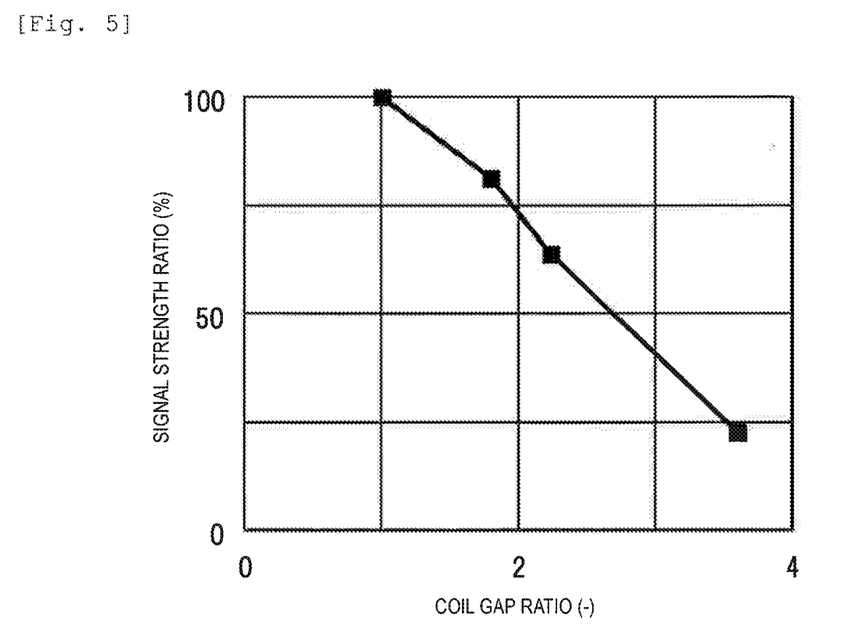
FIG. 5 is a schematic diagram illustrating an example of a relationship of a coil gap ratio and a signal intensity ratio.

However, when a plurality of detection modes are set according to a defect direction using the multi-coil probe 110 in which the coil 112 is arranged at a fixed gap, the gap between the excitation coil and the detection coil is variously different depending on the detection mode. FIG. 5 is a schematic diagram illustrating an example of a relationship of a coil gap ratio and a signal intensity ratio. As understood from the diagram, the signal intensity ratio of the electromotive force signal reduces as the coil gap ratio increases which is a coil gap index.

Here, it is possible to correct the difference of the signal intensity caused by the difference of the coil gap in each detection mode by possessing a reduction ratio of the signal intensity in the eddy current flaw detector 200 due to the coil gap in advance.

Here, the detection mode of the present embodiment is described with reference to FIGS. 6 to 8. As shown in the drawings, the eddy current inspection device 1 is provided with the orthogonal detection mode, the first intersection detection mode, and the second intersection detection mode. Here, FIGS. 6 to 8 indicate only the arrangement of a portion of coils 112 out of the multi-coil probes 110 indicated in FIG. 2. In addition, the multi-coil probe 110 in the detection modes scans in the Y direction in the drawings.

Figure 6:
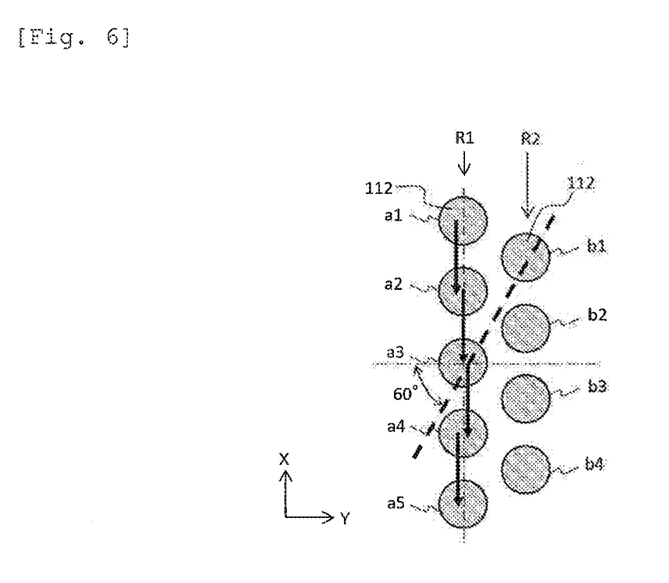
FIG. 6 is a schematic diagram for describing an orthogonal detection mode.

As shown in FIG. 6, the orthogonal detection mode is a mode in which the electromotive force signal is measured using the coil pair which is configured by the two coils 112 within the first row coil group R1. For example, in the mode, after performing measurement of the coil a1 as the excitation coil and the coil a2 as the detection coil, measurement is performed using the coil a2 as the excitation coil and the coil a3 as the detection coil, and measurement is performed below while switching the coils 112 in order within the first row coil group R1. The mode is superior in detection of the defect which develops in the X axis direction.

Figure 7:
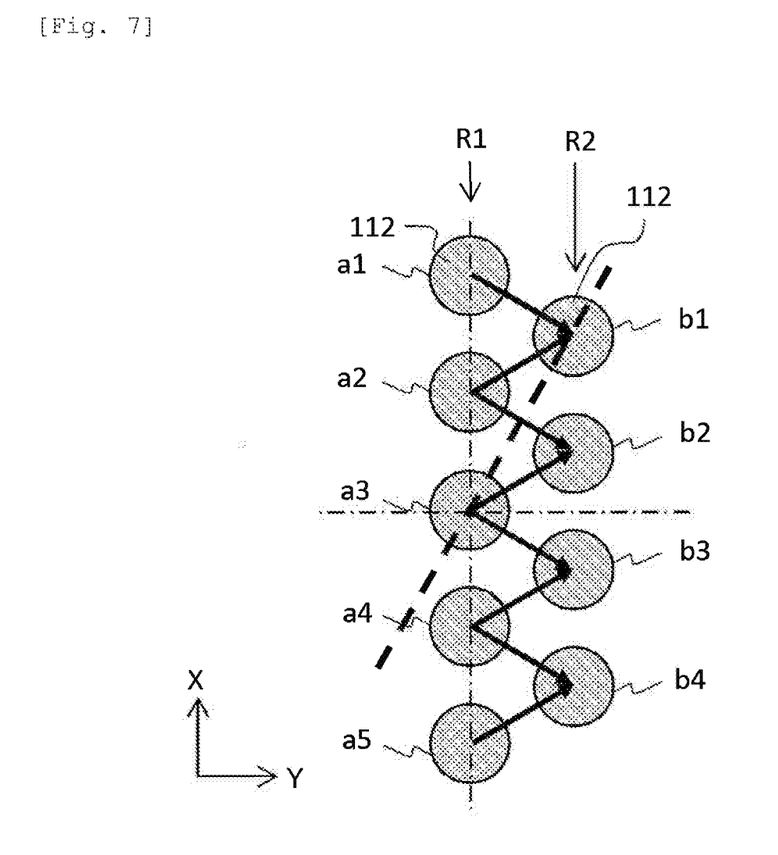
FIG. 7 is a schematic diagram for describing a first intersection detection mode.

As shown in FIG. 7, the first intersection detection mode is a mode in which the electromotive force signal is measured using the first coil pair which is configured by the two coils 112 in the first row and second row coil groups R1 and R2 lined up in a direction which intersects with the scanning direction. For example, in the mode, after performing measurement of the coil a1 as the excitation coil and the coil b1 as the detection coil, measurement is performed using the coil a2 as the excitation coil and the coil b1 as the detection coil. Subsequently, after performing measurement of the coil a2 as the excitation coil and the coil b2 as the detection coil, measurement is performed using the coil a3 as the excitation coil and the coil b2 as the detection coil, and measurement is performed in order below while switching between the coil 112 within the first row coil group R1 and the coil 112 within the second row coil group R2. The mode is superior in detection of the defect which develops in the Y axis direction.

Figure 8:
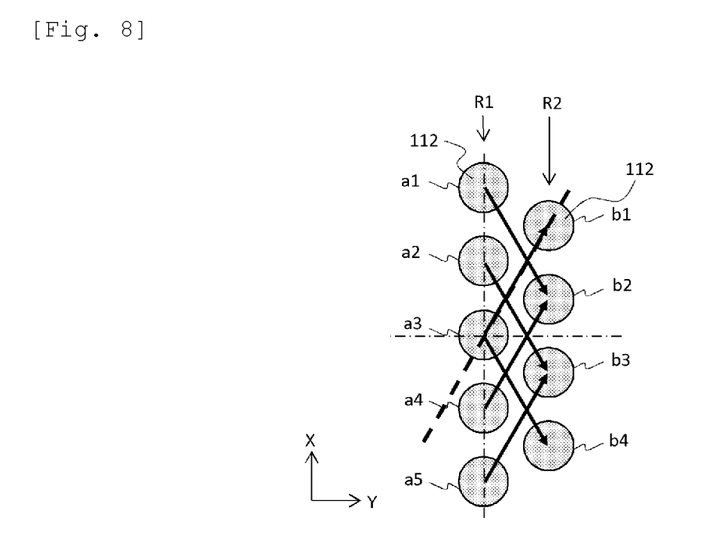
FIG. 8 is a schematic diagram for describing a second intersection detection mode.

As shown in FIG. 8, the second intersection detection mode is a mode in which a direction which intersects with the scanning direction is the same side as the direction through which the first coil pair intersects, and the electromotive force signal is measured using the second coil pair which is configured by the two coils 112 in the first row and second row coil groups R1 and R2 lined up in a direction which has a coil pair intersection angle which is larger than the coil pair intersection angle of the first coil pair. The mode is different from the first intersection detection mode in that how the excitation coil and the detection coil are combined. For example, in the mode, after performing measurement of the coil a1 as the excitation coil and the coil b2 as the detection coil, measurement is performed using the coil a3 as the excitation coil and the coil b1 as the detection coil. Subsequently, after performing measurement of the coil a2 as the excitation coil and the coil b3 as the detection coil, measurement is performed using the coil a4 as the excitation coil and the coil b2 as the detection coil, and measurement is performed in order below while switching between the coil 112 within the first row coil group R1 and the coil 112 within the second row coil group R2. The mode is superior in detection of the defect which develops in an oblique direction with respect to the Y axis.

Here, switching between the orthogonal detection mode, the first intersection detection mode, and the second intersection detection mode described above and selection of the excitation coil and the detection coil in each mode are performed by a program operation of the multiplexer circuit section 113.

In this manner, as shown in FIGS. 6 to 8, in a case where each coil 112 is disposed so as to be positioned in each vertex in a virtual equilateral triangle by the eddy current inspection device 1 being provided with the orthogonal detection mode, the first intersection detection mode, and the second intersection detection mode, the maximum defect intersection angle is 15°. These are half values of a maximum defect intersection angle of 30° which is obtained in the eddy current inspection device in the related art in which only two detection modes of the orthogonal detection mode and the first intersection detection mode are provided. When these are applied to the material N which is shown in FIG. 4(b), since the signal intensity is approximately 65% in the defect intersection angle 15° with respect to the signal intensity which is approximately 25% in the defect intersection angle 30°, distinction of a signal and noise becomes clear and it is possible to reliably identify the defect. Here, the coil gap in the second intersection detection mode is $\sqrt{3}$ times in comparison to the first intersection detection mode, but it is possible to obtain a signal of the corrected strength by compensating using the signal intensity compensation section 308.

[Defect Determination Method]

Determination of the defect is performed in two stages. As first stage, the signal intensity is used. In detail, first, the reference signal is acquired by measuring the reference defect in advance, and a maximum value A1 is obtained from the acquired reference signal. Here, the signal intensity is not large in comparison to the reference defect since defects that are actually generated are not clear conditions as the reference defect. Here, a coefficient $\alpha$ is multiplied by the maximum value A1 of the signal, and is set as a reference value A0 ($=\alpha \times$A1) of the defect determination.

Figure 9A:
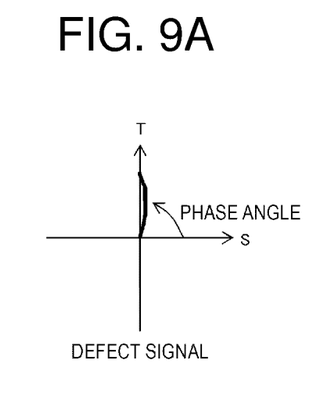
Figure 9B:
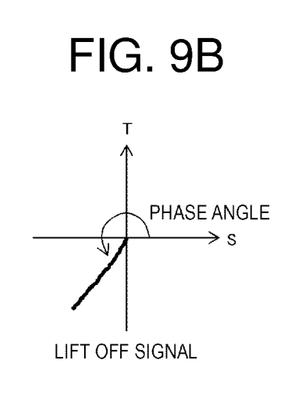

As the second stage, the defect signal and the noise signal are identified based on the phase change of the electromotive force signal with respect to the control signal. The phase change is evaluated using the Lissajous waveform. FIG. 9 shows schematic explanatory diagrams of a Lissajous waveform which is obtained using the eddy current inspection device in FIG. 1, and (a) indicates an example of the electromotive force due to the defect and (b) indicates an example of the electromotive force signal due to lift-off. In FIGS. 9(a) and (b), a horizontal axis indicates the signal intensity of a control signal S and a vertical axis indicates the signal intensity of an electromotive force signal T, and thereby it is possible to represent a phase angle between the control signal S and the electromotive force signal T. Typically, a phase of the reference defect is set such that the phase angle of the electromotive force signal T is 90° with respect to the control signal S. For this reason, the phase angle of the Lissajous waveform due to the defect is approximately 90° as in a thick solid line which is illustrated in FIG. 9(a). In contrast to this, the phase angle of a lift-off signal which is one type of noise (noise which is generated by separation of the multi-coil probe 110 from the subject s) is approximately 225° as in a thick solid line which is illustrated in FIG. 9(b).

Accordingly, for example, in a case where a signal intensity A of the electromotive force signal is a reference value A0 or more in any one of the orthogonal detection mode, the first intersection detection mode, or the second intersection detection mode, and the phase angle of the Lissajous waveform of the electromotive force signal is in the vicinity of 90°, it is possible to determine that the electromotive force signal is derived from the defect. In addition, the signal intensity A of the electromotive force signal is the reference value A0 or more, but in a case where the phase angle of the Lissajous waveform of the electromotive force signal is not in the vicinity of the phase angle 90°, it is possible to determine that there is noise in the electromotive force signal.

Subsequently, the operation method of the eddy current inspection device 1 is described. Here, the operation method of the eddy current inspection device 1 is not limited only to the method indicated below.

Figure 10:
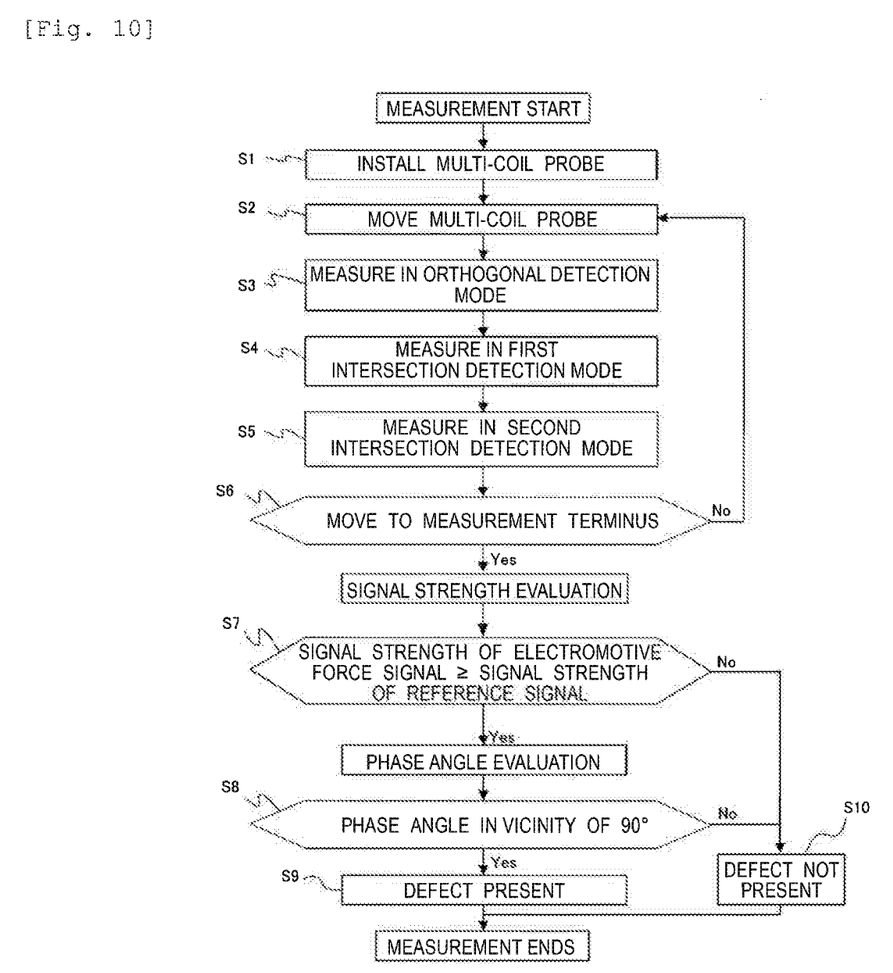
FIG. 10 is a schematic flow chart of a measurement in which the eddy current inspection device in FIG. 1 is used.

FIG. 10 is a schematic flow chart of a measurement in which the eddy current inspection device in FIG. 1 is used. Here, the control process which is described here is executed based on a program which is stored in advance in an internal memory of the multiplexer circuit section 113, the eddy current flaw detector 200, and the probe movement controller 300.

First, preparation for measurement is performed prior to the measurement. In the preparation, the signal (eddy current) of the reference defect which is formed of a material of the same subject s is measured in advance, and the obtained signal is stored in the eddy current flaw detector 200 as the reference signal. In addition, in the preparation, a dimension value which relates to the coil gap between the multi-coil probes 110 is input and stored in the eddy current flaw detector 200.

Thereafter, the multi-coil probe 110 is installed in the measurement start position of the subject s, and in intervention of the buffer material 150, the multi-coil probe 110 is pressed on the subject s using the probe pressing jig 140. At this time, the electromotive force signal in a normal state (state in which there is no defect) with respect to the subject s is measured and the coil calibration is performed, and the electromotive force signal of the state is stored (step S1).

The signal from the probe movement controller 300 is transmitted and the probe movement unit 120 is operated, and thereby the multi-coil probe 110 is moved (step S2).

Measurement is performed in the three detection modes described above. In detail, first, after measurement is performed (step S3) in the orthogonal detection mode, measurement (step S4) is performed in the first intersection detection mode and measurement (step S5) is performed in the second intersection detection mode in this order.

After the measurement ends in the three detection modes, determination is performed of whether or not the multi-coil probe 110 is moved to a measurement end position (step S6). In the determination result, in a case where the multi-coil probe 110 is not moved to the measurement end position, furthermore, the multi-coil probe 110 is moved and eddy current measurement is repeated, and in a case where the multi-coil probe 110 is moved to the measurement end position, the process transitions to the signal intensity evaluation which will be described later.

In the signal intensity evaluation, first, comparison of the signal intensity of the electromotive force signal and the signal intensity of the reference signal is performed (step S7). The evaluation determines large and small with respect to the reference value A0 of the defect determination as described in the defect determination method described above. At that time, in a case where the signal intensity A of the electromotive force signal is A<A0, since it is determined that there is no significant signal, after it is determined that there is no defect (step S10), measurement ends. Meanwhile, in a case where the signal intensity A of the electromotive force signal is A≥A0, since it is determined that there is a significant signal, the process transitions to the phase angle evaluation which will be described later.

In the phase angle evaluation, first, the Lissajous waveform described above is drawn and the phase angle of the electromotive force signal is calculated, and determination is performed of whether or not the obtained phase angle matches the defect characteristic. In detail, each electromotive force signal which is obtained in the orthogonal detection mode, the first intersection detection mode, and the second intersection detection mode is used and determination is performed of whether or not the phase angle of the Lissajous waveform is in the vicinity of 90° (step S8). At that time, in a case where none of the phase angles of all three detection modes is in the vicinity of 90°, since it is determined that there is no significant signal, after it is determined that there is no defect (step S10), measurement ends. Meanwhile, in a case where the phase angle of at least one of the three detection modes is in the vicinity of 90°, since it is determined that there is a significant signal, after it is determined that there is a defect (step S9), measurement ends.

Second Embodiment

Figure 11A:
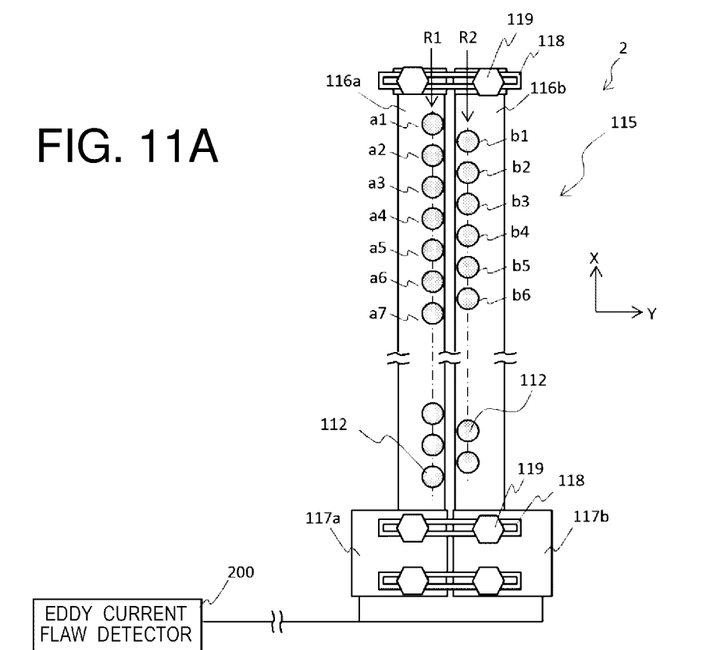
Figure 11B:
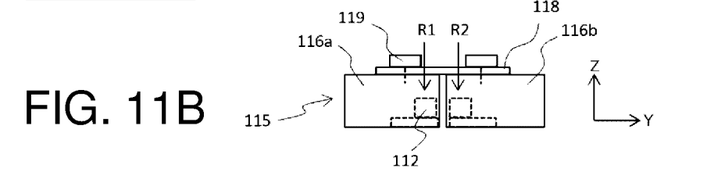

FIG. 11 shows schematic enlarged views of the multi-coil probe in the eddy current inspection device according to a second embodiment of the present invention. An eddy current inspection device 2 is different from the first embodiment in a point in which the gap between the first row coil group R1 and the second row coil group R2 in the multi-coil probe 115 is adjustable. Here, in the second embodiment, since the configuration other than the multi-coil probe 115 is similar to the first embodiment described above, detailed description thereof is omitted. In addition, since the detection mode, the defect determination method, and the operation method in the second embodiment are similar to the first embodiment described above, detailed description thereof is omitted.

As shown in FIG. 11, the multi-coil probe 115 is schematically configured by a first substrate 116a and a second substrate 116b.

The first substrate 116a disposes the coil 112 which configures the first row coil group R1 and a first multiplexer circuit section 117a, the first substrate 116a, the coil 112, and the first multiplexer circuit section 117a are electrically connected by wire, and the first multiplexer circuit section 117a is connected to the eddy current flaw detector 200. In addition, the second substrate 116b disposes the coil 112 which configures the second row coil group R2 and a second multiplexer circuit section 117b, the second substrate 116b, the coil 112, and the second multiplexer circuit section 117b are electrically connected by wire, and the second multiplexer circuit section 117b is connected to the eddy current flaw detector 200.

In addition, the multi-coil probe 115 connects the first substrate 116a and the second substrate 116b described above via a coil gap adjustment guide 118, and is fixed by an adjustment screw 119 such that it is possible to adjust a gap between the first row coil group R1 and the second row coil group R2 according to necessity.

Here, a setting method of the coil gap in the eddy current inspection device 2 is indicated. For example, in a case where the defect which is generated in the oblique direction in the material N described above is measured such that a value of 50% of a signal intensity of the reference defect is obtained, the defect intersection angle which is 50% is approximately 20° based on measurement data in FIG. 4(b). For this reason, the gap between the first row coil group R1 and the second row coil group R2 may be adjusted such that an angle between the X axis direction and the coil pair direction of the second intersection detection mode is 40°. That is, the gap may be adjusted so as to be 1.25 times (=1.5×tan 40°) with respect to how the gap between the adjacent coils 112 configure the first row coil group R1.

In this manner, the eddy current inspection device 2 is able to appropriately reduce the maximum defect intersection angle and is able to reliably detect the defect by controlling the sensitivity decrease by the gap between the first row coil group R1 and the second row coil group R2 in the multi-coil probe 115 being adjustable. In addition, according to the eddy current inspection device 2, since the adjustment of the coil pair intersection angle is possible, there is an advantage in that the plurality of multi-coil probes 115 in which the coil pair intersection angles are different are prepared according to the material and the like of the subject s, and in that switching is not necessary.

Here, the eddy current inspection device according to the present invention is not limited to the configuration in the embodiments described above, is indicated by the claims, and all modifications with a meaning equivalent to and within the scope of the claims are intended to be included.

For example, in the embodiments described above, the eddy current inspection devices 1 and 2 are described in which the multi-coil probes 110 and 115 are provided that have a coil group lined up in two rows in the linear direction which is orthogonal to the scanning direction, but the eddy current inspection device may be provided with a multi-coil probe that has a coil group which is lined up in three rows or four rows or more. In this case, it is possible to select the first row coil group and the second row coil group from the coil groups.

In addition, in the embodiments described above, in the first and second intersection detection modes, the eddy current inspection devices 1 and 2 which have the specified coil pair intersection angles are described, but are not limited to the first coil pair and the second coil pair having the above relationship, and are not limited to the specified coil pair intersection angles.

REFERENCE SIGNS LIST s SUBJECT
1, 2 EDDY CURRENT INSPECTION DEVICE
R1 FIRST ROW COIL GROUP
R2 SECOND ROW COIL GROUP
100 MAIN BODY
110, 115 MULTI-COIL PROBE
111 SUBSTRATE
116a FIRST SUBSTRATE
116b SECOND SUBSTRATE
112 COIL
113 MULTIPLEXER CIRCUIT SECTION
117a FIRST MULTIPLEXER CIRCUIT SECTION
117b SECOND MULTIPLEXER CIRCUIT SECTION

120 PROBE MOVEMENT UNIT
200 EDDY CURRENT FLAW DETECTOR
300 PROBE MOVEMENT CONTROLLER
308 SIGNAL INTENSITY COMPENSATION SECTION
304 SIGNAL INTENSITY MEASUREMENT SECTION
305 SIGNAL PHASE EVALUATION SECTION
400 DISPLAY UNIT

The invention claimed is:

1. An eddy current inspection device comprising:
a multi-coil probe having a first row coil group and a second row coil group, wherein the first row coil group includes a plurality of coils arranged in a first linear direction that is orthogonal relative to a scanning direction and the second row coil group includes a plurality of coils arranged in a second linear direction parallel to the first linear direction of the first row coil group, the first row coil group being disposed on a first substrate together with a first multiplexer circuit section and the second row coil group being disposed on a second substrate together with a second multiplexer circuit section; and
an eddy current flaw detector, to which the first and second multiplexer circuit sections are connected, the eddy current flaw detector comprising a detection mode control section configured to select a detection mode from:
an orthogonal detection mode which measures an electromotive force signal via a coil pair comprising two coils within the first row coil group, wherein the two coils include an excitation coil and a detection coil;
a first intersection detection mode which measures the electromotive force signal via a first coil pair comprising two coils within the first row coil group and the second row coil group that are lined up in a direction that intersects the scanning direction at a first coil pair intersection angle, wherein the two coils include an excitation coil and a detection coil, and
a second intersection detection mode which measures the electromotive force signal via a second coil pair comprising two coils within the first row coil group and the second row coil group that are lined up in a direction that intersects the scanning direction at a second coil pair intersection angle, wherein the second coil intersection angle is larger than the first coil pair intersection angle, and wherein the two coils include an excitation coil and a detection coil;
wherein the eddy current flaw detector further comprises a defect determination section configured to detect a presence or absence of a defect based on the electromotive force signal measured in the selected detection mode,
wherein the multi-coil probe connects the first and second substrates via a coil gap adjustment guide and is fixed by an adjustment screw such that a gap between the first and second row coil groups is adjustable, and
wherein the eddy current inspection device is configured to adjust the gap between the first and second row coil groups to reduce a maximum defect intersection angle so as to detect the defect reliably.

2. The eddy current inspection device according to 1, further comprising:
a signal intensity measurement section configured to determine the presence or absence of the defect based on a maximum value of a signal intensity of the electromotive force signal and a predetermined reference value.

3. The eddy current inspection device according to claim 2, further comprising:
a signal phase evaluation section configured to determine the presence or absence of the defect based on a phase angle of the electromotive force signal with respect to the reference signal.

4. The eddy current inspection device according to claim 1,
wherein the coils in the first row and second row coil groups are disposed in a zig-zag shape in planar view.

5. The eddy current inspection device according to claim 1, further comprising:
a signal intensity compensation section configured to perform a correction of the electromotive force signal based on a gap between the two coils in the orthogonal detection mode, the first and second coils in the first intersection detection mode, and the third and fourth coils in the second intersection detection mode.

* * * * *